US008197839B2

(12) United States Patent
Martinod et al.

(10) Patent No.: US 8,197,839 B2
(45) Date of Patent: Jun. 12, 2012

(54) SUSTAINED RELEASE DELIVERY SYSTEM

(75) Inventors: Serge R. Martinod, Groton, CT (US); Malcolm Brandon, Bulleen (AU)

(73) Assignee: Virbac Corporation, Fort Worth, TX (US)

( * ) Notice: Subject to any disclaimer, the term of this patent is extended or adjusted under 35 U.S.C. 154(b) by 1620 days.

(21) Appl. No.: 10/482,335

(22) PCT Filed: Jul. 1, 2002

(86) PCT No.: PCT/AU02/00866
§ 371 (c)(1),
(2), (4) Date: Jun. 29, 2004

(87) PCT Pub. No.: WO03/009833
PCT Pub. Date: Feb. 6, 2003

(65) Prior Publication Data
US 2004/0247643 A1    Dec. 9, 2004

(30) Foreign Application Priority Data

Jun. 29, 2001  (AU) ........................ PR6024

(51) Int. Cl.
*A61F 2/00* (2006.01)
(52) U.S. Cl. .................................... 424/426
(58) Field of Classification Search .......... 424/464, 424/469, 471, 474, 463; 604/506
See application file for complete search history.

(56) References Cited

U.S. PATENT DOCUMENTS

| 3,279,996 | A | * | 10/1966 | Long, Jr. et al. | 424/424 |
| 3,845,770 | A | * | 11/1974 | Theeuwes et al. | 424/427 |
| 3,916,899 | A | * | 11/1975 | Theeuwes et al. | 424/424 |
| 4,013,785 | A | * | 3/1977  | Weintraub et al. | 424/465 |
| 4,111,202 | A | * | 9/1978  | Theeuwes | 604/892.1 |
| 4,331,652 | A |   | 5/1982  | Ludwig et al. | |
| 4,578,075 | A | * | 3/1986  | Urquhart et al. | 604/892.1 |
| 4,681,583 | A | * | 7/1987  | Urquhart et al. | 424/454 |
| 4,777,033 | A |   | 10/1988 | Ikura et al. | 424/44 |
| 4,786,501 | A |   | 11/1988 | Janski et al. | 424/422 |
| 5,028,430 | A |   | 7/1991  | Sanders et al. | 424/423 |
| 5,034,229 | A | * | 7/1991  | Magruder et al. | 424/422 |
| 5,035,891 | A | * | 7/1991  | Runkel et al. | 424/423 |
| 5,211,951 | A | * | 5/1993  | Sparer et al. | 424/426 |
| 5,342,622 | A |   | 8/1994  | Williams et al. | |
| 5,744,163 | A | * | 4/1998  | Kim et al. | 424/489 |
| 5,788,977 | A |   | 8/1998  | Aguadisch et al. | 424/422 |
| 5,837,228 | A |   | 11/1998 | Shih et al. | 424/78.37 |
| 5,851,547 | A |   | 12/1998 | Fujioka et al. | 424/426 |
| 6,645,192 | B2 | * | 11/2003 | Kenison et al. | 604/506 |

FOREIGN PATENT DOCUMENTS

| EP | 0 462 959      | 12/1991 |
| EP | 0462959        | 1/1996  |
| EP | 0 990 450      | 4/2000  |
| EP | 0 990 450 A2   | 4/2000  |
| EP | 1112739 A1 *   | 7/2001  |
| JP | 64-045318      | 3/1989  |
| JP | 4-504122       | 7/1992  |
| JP | 04-230210      | 8/1992  |
| JP | 4-230621       | 8/1992  |
| JP | 5-500620       | 2/1993  |
| JP | 6-321803       | 11/1994 |
| JP | 9-225040       | 9/1997  |
| JP | 11-508224      | 7/1999  |
| JP | 01-500899      | 1/2001  |
| JP | 2001-199879    | 7/2001  |
| WO | WO 87/00139    | 1/1987  |
| WO | WO 90/11070    | 10/1990 |
| WO | WO 90/15637    | 12/1990 |
| WO | WO 92/02211    | 2/1992  |
| WO | WO 92/07556    | 5/1992  |
| WO | WO 95/17881    | 7/1995  |
| WO | WO 99/15166    | 4/1999  |
| WO | WO 99/51201 A1 | 10/1999 |
| WO | WO 00/03660 A1 | 1/2000  |
| WO | WO 00/13666 A1 | 3/2000  |
| WO | WO 00/18374 A1 | 4/2000  |
| WO | WO 01/10421 A1 | 2/2001  |
| WO | WO 01/34112    | 5/2001  |
| WO | WO 01/37811    | 5/2001  |
| WO | WO 01/37811 A1 | 5/2001  |
| WO | WO 01/76558 A1 | 10/2001 |

OTHER PUBLICATIONS

Author unknown, "Abamectin," The Merck Index, 12th Edition, Budavari, S. et al., Eds., Merck Research Laboratories Division of Merck & Co. Inc., Whitehouse Station, NJ, USA, Entry 1 (1996).
Author unknown, "Implants," Remington: The Science and Practice of Pharmacy, 19th Edition, Gennaro, A.R., Ed., Mack Publishing Company, Easton, PA, USA, pp. 1671-1672 (1995).
Cardamone, M., et al.: "Sustained-Release Delivery System and Their Application for Endoparasite Control in Animals", Journal of Controlled Release, vol. 51(1), pp. 73-83, 1998.
Cardamone et al., "Sustained-release delivery systems and their application for endoparasite control in animals", Journal of Controlled Release, 1998, 51, pp. 73-78.
Japanese Notice of Reasons for Rejection (original Japanese language and English language translation) for JP Patent Application No. 2003-515226 (mailing date: Jul. 6, 2010).
Office Action in corresponding Canadian Patent Application No. 2,452,075 (dated Feb. 2, 2011).

\* cited by examiner

*Primary Examiner* — Kamal Saeed
*Assistant Examiner* — Kristin Bianchi
(74) *Attorney, Agent, or Firm* — Morgan, Lewis & Bockius LLP

(57) ABSTRACT

A sustained release apparatus including at least one sustained release mini tablet implant; the or each mini tablet implant including a pharmaceutically active composition including at least one pharmaceutically active component; and a carrier therefor, wherein the or each tablet implant is of the coated tablet or covered rod type; the or each mini tablet implant being approximately 0.1 to 0.5 times the length and/or diameter of a single immediate release tablet capable of providing the desired threshold blood level depending on the pharmaceutical active selected, and having a payload of approximately 30% to 70% by weight of the total payload of an equivalent immediate release treatment conducted for an equivalent period; the sustained release apparatus providing, in use, zero order release of pharmaceutical active.

22 Claims, No Drawings

SUSTAINED RELEASE DELIVERY SYSTEM

CROSS REFERENCE TO RELATED APPLICATIONS

This application is a 371 filing of PCT/AU02/00866 filed Jul. 1, 2002, which claims priority to Australian Patent Application No. PR 6024, filed on Jun. 29, 2001, each of which are herein incorporated by reference in their entireties.

The present invention relates to a sustained release pharmaceutical composition, and in particular a sustained release composition in a tabletted, preferably mini-tablet form. More specifically, the present invention relates to a sustained release pharmaceutical composition which provides a significant increase in pharmaceutical payload.

A number of drug delivery systems are known in the prior art. However, where a disease indication requires the achievement of a high threshold blood plasma level and/or requires the delivery of multiple pharmaceuticals and/or requires sustained release to be continued over an extended period at high levels, the drug delivery systems known in the prior art generally exhibit insufficient drug carrying capacity.

Whilst it is theoretically possible to increase the amount of active delivered by increasing the size of the drug delivery systems in one or more dimensions (e.g. length or diameter), this may not achieve the anticipated result, e.g. as this may lead to "dose dumping" which may be harmful or even lethal to the animal to be treated. Alternatively the large size of the apparatus may prevent its use even with relatively large animals, in particular cattle.

For example, such drug delivery implants may be placed subcutaneously in the ear of an animal. This may be physically impossible where the size of the implant becomes too large.

Further, it has been found that use of multiple implants does not provide the required threshold blood level of pharmaceutical required to successfully treat the disease indication to be treated. This also is limiting due to the total bulk of the implants used.

It is, accordingly, an object of the present invention to overcome or at least alleviate one or more of the difficulties and deficiencies related to the prior art.

Accordingly, in a first aspect, there is provided a sustained release apparatus including at least one sustained release mini tablet implant;
the or each mini tablet implant including
a pharmaceutically active composition including
at least one pharmaceutically active component; and
a carrier therefor; and
optionally a sustained release support material, the pharmaceutically active composition being carried in or on the sustained release support material, when present;
the or each implant together being of significantly reduced size and/or payload relative to an equivalent immediate release treatment.

Applicants have surprisingly found that the sustained release apparatus according to the present invention requires significantly less pharmaceutical active than the equivalent immediate release treatment.

Preferably the or each implant has a payload of approximately 30 to 70%, preferably approximately 30 to 50% by weight, of the payload of an equivalent immediate release treatment. For example, for treatment of a pig with a porcine somatotropin (rPST), the recommended daily dosage regimen for injection of growth hormone may be approximately 5 mg/day or 35 mg over the course of 1 week. The sustained release apparatus according to the present invention may provide equivalent results with a mini tablet implant including approximately 12 mg of rPST. This may provide a sustained release profile for approximately 1 week.

Similarly, in a preferred embodiment of the present invention, where a plurality of sustained release mini tablet implants are included, each mini tablet may be of insufficient size and/or payload individually to provide a predetermined required threshold blood level of pharmaceutical active for treatment of a selected indication.

Applicants have surprisingly found, in this embodiment, that the threshold blood level of a pharmaceutical active required to treat a particular indication, e.g. a disease indication, may be achieved utilising a plurality of mini tablet implants which individually may not be of substantial value in treating the indication.

Preferably the sustained release apparatus may provide approximately zero order release of pharmaceutical active.

Each sustained release mini-tablet implant according to the present invention may be biodegradable.

Each sustained release mini-tablet implant according to the present invention may be of the uncoated or coated tablet (caplet), an uncovered or covered rod or matrix type. A tablet or rod-like shape is preferred. A compressed tablet or extruded rod bearing a silicone coating thereover may be used. A compressed tablet is particularly preferred.

For example each sustained release mini-tablet implant may be approximately 0.1 to 0.5 times, preferably approximately 0.20 to 0.25 times, the length and/or diameter of a single immediate release tablet, depending on the pharmaceutical active selected, and capable of providing the desired threshold blood level.

In a preferred form, there is provided a sustained release kit including
at least one sustained release mini tablet implant packaged for delivery in a single treatment;
the or each mini tablet implant including
a pharmaceutically active composition including
at least one pharmaceutically active component; and
a carrier therefor,
optionally a sustained release support material; the pharmaceutically active composition being carried in, or on, the sustained release support material, when present;
the or each implant together being of significantly reduced size and/or payload relative to an equivalent immediate release treatment.

Preferably each mini tablet implant has a payload of approximately 30 to 70% by weight of the total payload of an equivalent immediate release treatment for an equivalent period.

In a preferred embodiment, where a plurality of sustained release mini tablet implants are present, each mini tablet implant is of sufficient size and/or payload individually to provide a predetermined required threshold blood level of pharmaceutical active for treatment of a selected indication.

Optionally the sustained release kit according to this aspect of the present invention further includes a delivery apparatus.

For example, in veterinary applications, an injector instrument for subcutaneous or intramuscular delivery of standard size pellets may be used as the delivery apparatus.

The multiple mini-tablet implants may be provided in a single cartridge for use in a standard injector instrument which in turn disperse as individual mini-tablets within the body of the animal to be treated.

In a further preferred form of the present invention, the multiple mini-tablet implants may be packaged in a biodegradable sheath. The biodegradable sheath may be formed of a water-soluble material.

The water-soluble material utilised in the biodegradable sheath may be selected from one or more of the water-soluble substances described below.

Such a multi mini-tablet system permits the treatment of diseases or other indications over an extended period with pharmaceutically active components which have heretofore not been applicable to such indications as it has not been possible to achieve the required threshold blood plasma levels to be efficacious and to maintain those blood levels over an extended period of time.

For example, in veterinary applications, the pharmaceutically active component may be an anthelmintic, preferably a macrocyclic lactone, e.g. ivermectin, moxidectin, eprinomectin, doramectin and mixtures thereof. Ivermectin is preferred.

Ivermectin is a mixture of not less than 90% Ivermectin $H_2B_1a$ and not more than 5% Ivermectin $H_2B_1b$ having the respective molecular weights 875.10 and 861.07. Ivermectin is a potent macrocyclic lactone disaccharide antiparasitic agent used to prevent and treat parasite infestations in animals. The compound has activity against both internal and external parasites as well as being effective against arthropods, insects, nematodes, filarioidea, platyhelminths and protozoa.

The pharmaceutically active composition, as described above, includes at least one pharmaceutically active component. The pharmaceutically active component may be exemplified by, but not limited to, one or more selected from the group consisting of:

| | |
|---|---|
| Acetonemia preparations | Anabolic agents |
| Anaesthetics | Analgesics |
| Anti-acid agents | Anti-arthritic agents |
| Antibodies | Anti-convulsivants |
| Anti-fungals | Anti-histamines |
| Anti-infectives | Anti-inflammatories |
| Anti-microbials | Anti-parasitic agents |
| Anti-protozoals | Anti-ulcer agents |
| Antiviral pharmaceuticals | Behaviour modification drugs |
| Biologicals | Blood and blood substitutes |
| Bronchodilators and expectorants | Cancer therapy and related pharmaceuticals |
| Cardiovascular pharmaceuticals | Central nervous system pharmaceuticals |
| Coccidiostats and coccidiocidals | Contraceptives |
| Contrast agents | Diabetes therapies |
| Diuretics | Fertility pharmaceuticals |
| Growth hormones | Growth promoters |
| Hematinics | Hemostatics |
| Hormone replacement therapies | Hormones and analogs |
| Immunostimulants | Minerals |
| Muscle relaxants | Natural products |
| Nutraceuticals and nutritionals | Obesity therapeutics |
| Ophthalmic pharmaceuticals | Osteoporosis drugs |
| Pain therapeutics | Peptides and polypeptides |
| Respiratory pharmaceuticals | Sedatives and tranquilizers |
| Transplantation products | Urinary acidifiers |
| Vaccines and adjuvants | Vitamins |

The pharmaceutically active component may include a water-insoluble pharmaceutical, a water-soluble pharmaceutical or mixtures thereof.

The water-soluble pharmaceutical actives useful in the sustained release composition according to the present invention include such drugs as peptides, polypeptides, proteins, glycoproteins, polysaccharides, and nucleic acids.

The present invention is particularly appropriate for pharmaceuticals that are very active even in extremely small quantities and whose sustained long-term administration is sought. When used in substantially increased quantifies, such pharmaceuticals may be applied to disease indications heretofore untreatable over an extended period. The pharmaceuticals may be exemplified by, but not limited to, one or more selected from the group consisting of cytokines (eg. interferons and interleukins), hematopoietic factors (eg. colony-stimulating factors and erythropoletin), hormones (eg. growth hormone, e.g. recombinant porcine somatotropin rPST, growth hormone releasing factor, calcitonin, leuteinizing hormone, leuteinizing hormone releasing hormone, and insulin), growth factors (eg. somatomedin, nerve growth factor, neurotrophic factors, fibroblast growth factor, and hepatocyte proliferation factor); cell adhesion factors; immunosuppressants; enzymes (eg. asparaginase, superoxide dismutase, tissue plasminogen activating factor, urokinase, and prourokinase), blood coagulating factors (eg. blood coagulating factor VIII), proteins involved in bone metabolism (eg. BMP (bone morphogenetic protein)), and antibodies.

A growth hormone, e.g. recombinant porcine somatotropin is particularly preferred.

A cytokine, e.g. interferon, is also particularly preferred.

The interferons may include alpha, beta, gamma, or any other interferons or any combination thereof. Likewise, the interleukin may be IL-1, IL-2, IL-3, or any others, and the colony-stimulating factor may be multi-CSF (multipotential CSF), GM-CSF (granulocyte-macrophage CSF), G-CSF (granulocyte CSF), M-CSF (macrophage CSF), or any others.

Vaccines are also particularly preferred. The vaccines useful in the sustained release delivery apparatus according to the present invention may be exemplified by, but not limited to, one or more selected from the group consisting of

| | |
|---|---|
| Adenovirus | Anthrax |
| BCG | Chlamydia |
| Cholera | Circovirus |
| Classical swine fever | Coronavirus |
| Diphtheria-Tetanus (DT for children) | Diphtheria-Tetanus (tD for adults) |
| Distemper virus | DTaP |
| DTP | E coli |
| Eimeria (coccidosis) | Feline immunodeficiency virus |
| Feline leukemia virus | Foot and mouth disease |
| Hemophilus | Hepatitis A |
| Hepatitis B | Hepatitis B/Hib |
| Herpes virus | Hib |
| Influenza | Japanese Encephalitis |
| Lyme disease | Measles |
| Measles-Rubella | Meningococcal |
| MMR | Mumps |
| Mycoplasma | Para influenza virus |
| Parvovirus | Pasteurella |
| Pertussis | Pestivirus |
| Plague | Pneumococcal |
| Polio (IPV) | Polio (OPV) |
| Pseudorabies | Rabies |
| Respiratory syncitial virus | Rotavirus |
| Rubella | Salmonella |
| Tetanus | Typhoid |
| Varicella | Yellow Fever |

Pharmaceuticals that may be applied in pharmaceutically active compositions according to the present invention may be further exemplified by low-molecular-weight drugs such as water-soluble anticancer agents, antibiotics, anti-inflammatory drugs, alkylating agents, and immunosuppressants. Examples of these drugs include adriamycin, bleomycins, mitomycins, fluorouracil, peplomycin sulfate, daunorubicin hydrochloride, hydroxyurea, neocarzinostatin, sizofuran, estramustine phosphate sodium, carboplatin, beta-lactams, tetracyclines, aminoglycosides, and phosphomycin.

The pharmaceutically active composition of the present invention may contain two or more drugs depending on the disease or other indication and method of application.

For example, in veterinary applications for control of parasitic infections, a combination of ivermectin and praziquantel or a combination of zeranol and trembolone may be used.

Water-insoluble pharmaceutically active components which may be utilised in the sustained release delivery apparatus according to the present invention include lipophilic pharmaceuticals.

A lipophilic pharmaceutical may be any lipophilic substance so long as it is, as a form of a preparation, in a solid state at the body temperature of an animal or a human being to which the preparation is to be administered. The term "Lipophilic" as herein used means that the solubility of a substance in water is low, which specifically includes the following natures, as described in Pharmacopoeia of Japan 13th Edition (1996): practically insoluble (the amount of more than or equal to 10000 ml of solvent is required to dissolve 1 g or 1 ml of a solute), very hard to dissolve (the amount of more than or equal to 1000 ml and less than 10000 ml of solvent is required to dissolve 1 g or 1 ml of a solute), or hard to dissolve (the amount of more than or equal to 100 ml and less than 1000 ml of solvent is required to dissolve 1 g or 1 ml of a solute).

Specific examples of the lipophilic pharmaceutical include, but are not limited to, anti-parasiticides (e.g. avermectin, ivermectin, spiramycin), antimicrobials (eg. ceftiofur; amoxicillin, erythromycin, oxytetracycline, and lincomycin), anti-inflammatory agents (eg. dexamethasone and phenylbutasone), hormones (eg. levothyroxine), adrenocorticosteroids (eg. dexamethasone palmitate, triamcinolone acetonide, and halopredone acetate), non-steroidal anti-inflammatory agents (eg. indometacin and aspirin), therapeutic agents for arterial occlusion (eg. prostaglandin E1), anticancer drugs (eg. actinomycin and daunomycin), therapeutic agents for diabetes (eg. acetohexamide), and therapeutic agents for osteopathy (eg. estradiol).

Depending on the disease or method for application, multiple lipophilic drugs may be contained. In addition to the lipophilic drug having a direct therapeutic effect, the drug may be a substance with a biological activity, and such a substance as promotes or induces a biological activity, which includes an adjuvant for a vaccine, for example saponin. In such a case, incorporation of a vaccine into an implant results in a sustained release preparation of a vaccine with an adjuvant.

As stated above, the pharmaceutically active composition according to the present invention further includes a carrier for the pharmaceutically active component.

The pharmaceutical carrier may be selected to permit release of the pharmaceutically active component over an extended period of time from the composition.

The carrier may include a water-soluble substance.

A water-soluble substance is a substance which plays a role of controlling infiltration of water into the inside of the drug dispersion. There is no restriction in terms of the water-soluble substance so long as it is in a solid state (as a form of a preparation) at the body temperature of an animal or human being to which it is to be administered, and is a physiologically acceptable, water-soluble substance.

One water-soluble substance, or a combination of two or more water-soluble substances may be used. The water-soluble substance specifically may be selected from one or more of the group consisting of synthetic polymers (eg. polyethylene glycol, polyethylene polypropylene glycol), sugars (eg. sucrose, mannitol, glucose, sodium chondroitin sulfate), polysaccharides (e.g. dextran), amino acids (eg. glycine and alanine), mineral salts (eg. sodium chloride), organic salts (eg. sodium citrate) and proteins (eg. gelatin and collagen and mixtures thereof).

In addition, when the water-soluble substance is an amphipathic substance, which dissolves in both an organic solvent and water, it has an effect of controlling the release of, for example, a lipophilic pharmaceutical by altering the solubility thereof. An amphipathic substance includes, but not limited to, polyethylene glycol or a derivative thereof, polyoxyethylene polyoxypropylene glycol or a derivative thereof, fatty acid ester and sodium alkylsulfate of sugars, and more specifically, polyethylene glycol, polyoxy stearate 40, polyoxyethylene polyoxypropylene glycol, sucrose esters of fatty acids, sodium lauryl sulfate, sodium oleate, and sodium desoxycholic acid (sodium deoxycholate (DCA)).

Polyoxyethylene polyoxypropyleneglycol, sucrose, or a mixture of sucrose and sodium desoxycholic acid (or sodium deoxycholate) (DCA) are preferred.

In addition, the water-soluble substance may include a substance which is water-soluble and has any activity in vivo such as low molecular weight drugs, peptides, polypeptides, proteins, glycoproteins, polysaccharides, or an antigenic substance used as vaccines, i.e. water-soluble drugs.

The pharmaceutical carrier may constitute from approximately 1% to 30% by weight, preferably approximately 10% to 20% by weight of the total weight of the pharmaceutically active composition.

Each sustained release mini tablet implant may include additional carriers or excipients, lubricants, fillers, plasticisers, binding agent, pigments and stabilising agents.

Suitable fillers may be selected from the group consisting of talc, titanium dioxide, starch, kaolin, cellulose (microcrystalline or powdered) and mixtures thereof.

Suitable binding agents include polyvinyl pyrrolidine, hydroxypropyl cellulose and hydroxypropyl methyl cellulose and mixtures thereof.

The sustained release support material, when present, may take the form of a support matrix, tablet or rod, preferably a coated tablet structure.

The sustained release support material may be formed from a biodegradable or biocompatible material, preferably a biocompatible hydrophobic material. The biocompatible material may be selected from the group consisting of polyesters, polyamino acids, silicones, ethylene-vinyl acetate copolymers and polyvinyl alcohols. Preferably the sustained release support material is a silicone material. A silicone rod is preferred. The silicone material may be a porous silicon or Biosilicon material, for example as described in international patent application PCT/GB99/01185, the entire disclosure of which is incorporated herein by reference. A mesoporous, microporous or polycrystalline silicon or mixtures thereof may be used.

In a preferred aspect of the present invention the sustained release support material may include
a solid absorption medium; and optionally
a viscous polymer component.

The solid absorption medium may be a silicon material, e.g. a silicon material including one or more of a fumed silica and a porous silica. The pharmaceutical active may be introduced onto the solid absorption medium in the form of a solution, after which solvent may be removed.

The viscous polymer component when present may include a siloxane polymer.

Biodegradable polymers that may be employed in the present invention may be exemplified by, but not limited to, polyesters such as poly(lactic acid-glycolic acid) copolymers (PLGA), etc. and by hydrophobic polyamino acids such as polyaranin, polyleucine etc., polyanhydride, poly(glycerolsebacate) (PGS), Biopol, and the like. The hydrophobic polyamino acids mean polymers prepared from hydrophobic amino acids.

Nonbiodegradable polymers that may be employed in the present invention may be exemplified by, but not limited to, silicones, polytetrafluoroethylenes, polyethylenes, polypropylenes, polyurethanes, polyacrylates, polymethacrylates such as polymethylmethacrylates, etc., ethylene-vinyl acetate copolymers, and others.

The sustained release implant according to the present invention may be manufactured according to copending Australian provisional patent application PR7614 entitled "Preparation of sustained release pharmaceutical composition", to Applicants, the entire disclosure of which is incorporated herein by reference.

Sustained release implants according to the present invention may preferably have a double-layer structure, in order to achieve long-term zero-order release.

The inner layer of the pharmaceutical formulation of the present invention, viewed in right section, may contain two or more layers containing different water-soluble pharmaceuticals. These layers may take the form of concentric circles with a single center of gravity or may appear as a plural number of inner layers whose respective centers of gravity lie at different points in the cross section.

When the pharmaceutical formulation contains more than one inner layer there may be one or more pharmaceuticals present in the inner layers. For example, the pharmaceuticals may be present such that each layer contains a different pharmaceutical or there is more than one pharmaceutical in one or all of the inner layers.

The size of the pharmaceutical formulation of the present invention may, e.g. in the case of intramuscular administration, be relatively small, e.g. 0.1 to 0.5 times normal size. For example using an injector-type instrument, the configuration may be circular cylindrical, and the cross-sectional diameter in the case is preferably approximately 0.1 to 4 mm, the axial length being preferably approximately 0.1 to 20 mm, preferably approximately 0.25 to 5 mm, more preferably approximately 1 to 5 mm.

The thickness of the outer layer should be selected as a function of the material properties and the desired release rate. The outer layer thickness is not critical as long as the specified functions of the outer layer are fulfilled. The outer layer thickness is preferably 0.05 mm to 3 mm, more preferably 0.05 mm to 0.25 mm, and even more preferably 0.05 mm to 0.1 mm.

Applicants have further surprisingly found that it is possible to formulate certain macrocyclic lactones, including ivermectin, in a unit dosage, e.g. tablet or implant form.

Accordingly, in a further aspect of the present invention there is provided an anthelmintic pharmaceutical composition including an anthelmintic component; and
a non-silicone carrier therefor, in a unit dosage form.

The anthelmintic pharmaceutical composition may be utilised alone, or preferably in combination with the sustained release apparatus described above.

The anthelmintic pharmaceutical composition may be included as a further component in the sustained release kit as described above.

The anthelmintic component is preferably an insect growth regulator or a macrocyclic lactone, more preferably ivermectin.

The applicants have surprisingly found that a pharmaceutical composition may be formulated in a compressed or extruded tablet/implant form without the necessity to include a silicone component.

The pharmaceutical carrier may be the same as, or similar to, the pharmaceutical carriers utilised in the preparation of the mini tablet implants described above.

A water-soluble substance, or a combination of two or more water-soluble substances, is preferred. Sucrose, alkali metal, chloride (e.g. sodium chloride) or sodium deoxycholic acid or a mixture thereof are preferred carriers. A mixture of sucrose and sodium deoxycholic acid (DCA) is preferred.

The anthelmintic pharmaceutical composition may take the form of a compressed tablet or extruded rod, optionally a covered rod or tablet. A silicone coating may be applied to the tablet or rod. A mixture of covered and non-covered rod or tablets may be utilised to provide both immediate release and sustained release properties and/or to provide an initial and booster treatment, e.g. for vaccination, in a single treatment.

Applicants have further surprisingly found it is possible to formulate certain growth enhancing materials in a unit dosage, e.g. a tablet or implant form, which exhibit a sustained release profile.

Accordingly, in a still further aspect of the present invention there is provided a sustained release growth enhancing composition including a growth enhancing component; and
a non-silicone carrier therefor, in a unit dosage form.

The applicants have surprisingly found that a sustained release growth enhancing composition may be formulated in a compressed or extruded tablet/implant form without the necessity to include a silicone component.

The sustained release growth enhancing composition may be utilised alone, or preferably in combination with the sustained release apparatus described above.

The sustained release growth enhancing composition may be included as a further component in the sustained release kit as described above.

The growth enhancing component may be selected from one or more of the group consisting of hormones (eg. growth hormone, e.g. recombinant porcine somatotropin rPST, growth hormone releasing factor, calcitonin, leuteinizing hormone, leuteinizing hormone releasing hormone, and insulin), growth factors (eg. somatomedin, nerve growth factor, neurotrophic factors, fibroblast growth factor, and hepatocyte proliferation factor. A growth hormone, e.g. a natural or synthetic human, porcine, bovine, ovine or like growth hormone may be used. A recombinant porcine somatotropin (rPST) is preferred.

The pharmaceutical carrier may be the same as, or similar to, the pharmaceutical carriers utilised in the preparation of the mini tablet implants described above.

A water-soluble substance, or a combination of two or more water-soluble substances, is preferred. Sucrose, sodium chloride or sodium deoxycholic acid or a mixture thereof are preferred canters. Sodium chloride or a mixture of sucrose and sodium deoxycholic acid (DCA) is particularly preferred.

The sustained release growth enhancing composition may take the form of a compressed tablet or extruded rod, optionally a covered rod or tablet. A silicone coating may be applied to the tablet or rod, but is not essential.

The compressed tablet formulation may include suitable fillers or excipients as discussed above. A lubricant, such as magnesium stearate, is particularly preferred.

The growth enhancing composition may accordingly include
approximately 1% to 20% by weight alkali metal chloride;
approximately 0.5% to 5% by weight lubricant; and
approximately 75% to 97.5% by weight growth hormone.
Preferably the growth enhancing composition may include
approximately 5% to 15% by weight sodium chloride;
approximately 0.5% to 5% by weight magnesium stearate; and
approximately 80% to 94.5% by weight recombinant porcine somatotropin.

In a still further preferred aspect of the present invention the sustained release kit may further include
a plurality of sustained release mini-implants or pellets packaged for delivery in a single treatment;
each sustained release mini-implant or pellet including
a sustained release support material; and
a pharmaceutically active composition carried in, or on, the sustained release support material;
the pharmaceutically active composition including
at least one pharmaceutically active component; and
a carrier therefor;
each implant optionally of insufficient size individually to provide a predetermined desired threshold blood level of pharmaceutical active for treatment of a selected, e.g. disease, indication.

The sustained release mini-implants or pellets may be as described in copending Australian provisional patent application PR6025 entitled "Sustained release pharmaceutical composition", to Applicants, the entire disclosure of which is incorporated herein by reference.

The sustained release mini implants or pellets may be incorporated in the sustained release kit as a separate component and/or may be incorporated into the sustained release mini tablets as a single component.

In a further aspect of the present invention there is provided a method for the therapeutic or prophylactic treatment of an indication, preferably a disease indication, in an animal (including a human) requiring such treatment, which method includes administering to the animal a sustained release delivery apparatus including at least one sustained release mini tablet implant;
the or each implant including
a pharmaceutically active composition including
at least one pharmaceutically active component; and
a carrier therefor, and
optionally a sustained release support material; the pharmaceutically active composition being carried in or on the sustained release support material, when present;
the or each implant together being of significantly reduced size and/or payload relative to an equivalent immediate release treatment.

Preferably the or each mini tablet implant has a payload of approximately 30% to 70% by weight of the total payload of an equivalent immediate release treatment for an equivalent period.

In a further preferred embodiment, when a plurality of sustained release mini tablets implants are used, each implant is of insufficient size and/or payload individually to provide a predetermined required threshold blood level of pharmaceutical active for treatment of a selected indication.

As stated above, it has been found in this embodiment, that the pharmaceutical payload may be increased by the sustained release delivery apparatus according to the present invention when compared to the prior art. Diseases which were heretofore untreatable may now be treated over an extended period of time utilising the apparatus of the present invention.

For example, in animals suffering from parasitic infections such as ticks, the animals may be treated utilising the sustained release delivery apparatus including an anti-parasitic drug such a ivermectin. Heretofore, it was not possible to achieve a required blood concentration threshold to permit treatment of such a parasitic disease utilising a sustained release approach as the required blood concentration threshold could not be achieved utilising such a mechanism.

Similarly, for indications relating to growth, animals may be treated utilising the sustained release delivery apparatus including a growth enhancing component such as growth hormone including human, porcine, ovine and bovine growth hormones.

Heretofore, it was not possible to achieve a required blood concentration threshold to achieve enhanced growth over an extended period of time.

The method of administration may include subcutaneous or intramuscular injection, intraoccular or in the ear, intranasal insertion or indwelling, intravaginal or intradwelling, intrarectal insertion or indwelling, for example as a suppository or utilising oral administration.

The method of administration may be via use of the sustained release kit as described above.

The animals to be treated may be selected from the group consisting of sheep, cattle, goats, horses, camels, pigs, dogs, cats, ferrets, rabbits, marsupials, buffalos, yacks, primates, humans, birds including chickens, geese and turkeys, rodents including rats and mice, fish, reptiles and the like.

The method according to the present invention is particularly applicable to larger animals, e.g. cattle, sheep, pigs, dogs and humans where high dosage levels are required to achieve the prerequisite threshold pharmaceutical active blood levels for successful treatment of selected disease indications.

The present invention will now be more fully described with reference to the accompanying examples. It should be understood, however, that the description following is illustrative only and should not be taken in anyway as a restriction on the generality of the invention described above.

EXAMPLE 1

Laboratory-scale formulation of the ivermectin-Sucrose and Magnesium Stearate (lubricant) for the tableting was conducted as follows:
the "base-formulation" was weighed into a polyethylene terephthalate container (polyethylene lid), and the weight recorded;
the requisite amount of magnesium stearate was calculated and weighed into the polyethylene terephthalate container,
the formulation was mixed by tumbling for ca. 15 minutes;
tablets were prepared (details below); and
subsequent to tableting (described below), the tablets were placed in polyethylene sample vials, sealed, labelled (with the sample number, study number, type of sample, date collected, and storage conditions) and placed in storage (4° C.).

The Tableting Protocol Involved:
filling the tableting die cavity with powder,
compression of the powder;
repeat of the above steps until the requisite loading (ca. 5, 10, 30, 40, 60 and 70 mg) was achieved;

ejection of the full tablet (or parts thereof) from the die cavity by raising the lower punch.

Pressing pressure: ca 1200 psi

Conditions Temperature=20° C.

Humidity=ambient

Tablet Properties:

Dimension nominal 2.95 mm diameter×length (in mm) as required

Mass per tablet nominal 5 mg per 1.0 mm tablet

Results and Concluding Remarks:

Details of the tablet batches are provided in Table 1.

TABLE 1

| Batch ID # | Ivermectin-Sucrose mass (g) (% Ivermectin-Sucrose) | Mg Stearate mass (g) | Tablet data |
|---|---|---|---|
| 1 | 49.732 (97.02) | 1.529 | 2.6310 g tables (ca 449 tablets); average length = 1.02 mm/tablet; average mass = 5.86 mg/tablet; 5.75 mg formulation/mm; IVM 4.7 mg |
| 2 | | | 4.8155 g tables (ca 406 tablets); average length = 1.90 mm/tablet; average mass = 11.85 mg/tablet; 6.24 mg formulation/mm; IVM 9.48 mg |
| 3 | | | 13.7347 g tables (ca 420 tablets); average length = 4.80 mm/tablet; average mass = 32.74 mg/tablet; 6.82 mg formulation/mm; IVM 26.1 mg |
| 4 | | | 4.6395 g tables (ca 111 tablets); average length = 5.74 mm/tablet; average mass = 42.0 mg/tablet; 7.31 mg formulation/mm; IVM 33.6 mg |
| 5 | | | 6.2921 g tables (ca 109 tablets); average length = 7.82 mm/tablet; average mass = 57/78 mg/tablet; 7.39 mg formulation/mm; IVM 46.2 mg |
| 6 | | | 8.1602 g tables (ca 112 tablets); average length = 10.07 mm/tablet; average mass = 72.37 mg/tablet; 7.19 mg formulation/mm; IVM 57.9 mg |

All tablets were prepared using Scientec Tablet press (Tool #11). Some tablets, generally shorter length, exhibiting elastic memory from the compression process and were greater than specified length following relaxation/ejection from the press.

Addition of magnesium stearate to the base formulation was necessary to enable ready release of the tablet from the die (lengths greater than 2.0 mm length) and from the cup of the ejection punch (1 and 2 mm length tablets). For commercial production, routine methods of formulating and "tablet" production are necessary anticipated as being suitable for this formulation.

All tablets were off-white and "solid" under ambient conditions.

A number of tablets were then implanted into sheep via intra-muscular injection. The results are shown in Table 2, in particular the blood serum levels of ivermectin (mg/ml).

TABLE 2

| Pellet Size | Coated Dose IVM | | | Uncoated Dose IVM | | |
|---|---|---|---|---|---|---|
| | 12.5 mg | 25 mg | 50 mg | 12.5 mg | 25 mg | 50 mg |
| 1.9 mm | 0.21 | 0.62 | 0.62 | 0.20 | 0.82 | 3.00 |
| 4.8 mm | — | 0.35 | 0.49 | — | 0.37 | 1.67 |
| 10 mm | — | — | 0.53 | — | — | 3.26 |

12 groups—3 sheep/group (all intramuscular)
 —4 sheep in control group—EAR
 1 sheep—5 pellets×1.9 mm tablets
 1 sheep—2 pellets×4.8 mm tablets
 1 sheep—1 pellet×10 mm tablet
 1 sheep—True "0" control

EXAMPLE 2

Example 1 was repeated to produce a series of tablets of suitable size and payload for use with cattle.

Details of the tablet batches are provided in Table 3.

TABLE 3

| Calf No. | Dose IVM | Size | Mg/tablet | No of pellets | Total length |
|---|---|---|---|---|---|
| 1 | 100 mg | 1 mm | 4.7 | 21 | 21 mm |
| 2 | 100 mg | 1.9 mm | 9.5 | 11 | 21 mm |
| 3 | 100 mg | 4.8 mm | 26.1 | 4 | 19 mm |
| 4 | 100 mg | 5.7 mm | 33.6 | 3 | 17 mm |
| 5 | 100 mg | 7.8 mm | 46.2 | 3 | 23 mm |
| 6 | 100 mg | 10 mm | 57.9 | 2 | 20 mm |
| 7 | 0 | 0 | | | |

A number of tablets were then implanted into cattle via intra-muscular injection. The results are shown in Table 4, in particular the blood serum levels of ivermectin (mg/ml).

TABLE 4

| Calf No | Treatment No | Treatment | Weeks | | | | | | | |
|---|---|---|---|---|---|---|---|---|---|---|
| | | | 0 | 1 | 2 | 3 | 4 | 6 | 8 | 10 |
| 1 | 1 | 1 mm × 21 | ND | 4.9 | 4.9 | 2.8 | 2.2 | | | |
| 14 | 2 | 1.9 mm × 11 | ND | 2.9 | 1.7 | 1.0 | 1.0 | | | |
| 52 | 3 | 4.9 mm × 4 | ND | 1.6 | 1.8 | 1.1 | 0.85 | | | |
| 50 | 4 | 5.7 mm × 3 | ND | 4.8 | 2.3 | 1.1 | 0.70 | | | |
| 61 | 5 | 7.8 mm × 3 | ND | 2.3 | 1.9 | 1.1 | 0.91 | | | |
| 18 | 6 | 10 mm × 2 | ND | 24.6 | 13.3 | 5.2 | 3.2 | | | |
| 33 | 7 | Control | ND | ND | ND | ND | ND | | | |

ND = not detected

EXAMPLE 3

Laboratory-scale formulation of compressed tablet implants of recombinant porcine somatotropin (rPST).

The tableting procedure was similar to that described in Example 1. Sodium chloride (NaCl) is finely ground utilising a mortar and pestle prior to tableting.

Details of the tablet batches are provided in Table 5.

TABLE 5

| Batch ID | rPST-NaCl mass (g) (% rPST-NaCl) | Mg stearate mass (g) | Tablet data |
|---|---|---|---|
| 1 | 2.217 (97.3) Smart Tab M | 0.062 | 154 tablets average length = 3 mm/tablet average mass = 14.8 mg/tablet Pure rPST 13 mg/tablet |
| 2 | 2.325 (97.3) Smart Tab A | 0.065 | 144 tablets average length = 3.4 mm/tablet average mass = 16.6 mg/tablet Pure rPST 13 mg/tablet (PST only 90% pure) |

A number of the compressed tablets were implanted via sub-cutaneous injection in pigs. The results illustrating improved feed conversion efficiency, fat reduction, etc are shown in Table 6.

TABLE 6

| | | | 0-7 days | | |
|---|---|---|---|---|---|
| | No of Pigs | Implant size PST | Feed intake (kgs) | Weight increase (kgs) | FCR |
| Group 1 PST Injection A | 6 | 5 mg/day | 16.33 | 8.30 | 1.97 |
| Group 2 PST Injection M | 6 | 5 mg/day | 16.78 | 9.43 | 1.78 |
| Group 8 Sham Control | 6 | — | 17.18 | 6.03 | 2.85 |
| Group 4 Smart Tab M | 6 | 13 mg 3× per week | 13.95 | 7.53 | 1.85 |
| Group 5 Smart Tab A | 6 | 14 mg 3× per week | 16.77 | 8.00 | 2.10 |

EXAMPLE 3

The pig experiments illustrated in Example 2 were repeated over 7, 14 and 21 days with varying numbers of implants.

The results are shown in Tables 7 and 8.

TABLE 7

| | No pigs | Days | Implant size PST | Feed intake (kgs) | Weight increase (kgs) | FCR | P2 mm | P2 mm change |
|---|---|---|---|---|---|---|---|---|
| | | | | 0-7 days | | | | |
| Group 4 Smart Tab M | 6 | 0-7 | 3 × 13 mg | 13.95 | 7.53 | 1.85 | 10.2 | −0.1 |
| Group 5 Smart Tab A | 6 | 0-7 | 3 × 14 mg | 16.77 | 8.00 | 2.10 | 11.0 | +0.8 |
| Group 8 Sham Control | 6 | | — | 17.18 | 6.03 | 2.85 | 12.2 | +0.9 |
| | | | | 7-14 days | | | | |
| Group 4 Smart Tab M | 6 | 7-14 | 1 × 6.5 mg | 14.59 | 4.53 | 2.69 | 10.7 | +0.5 |
| Group 5 Smart Tab A | 6 | 7-14 | 3 × 14 mg | 17.68 | 7.27 | 2.43 | 12.2 | +1.2 |
| Group 8 Sham Control | 6 | | — | 18.10 | 6.63 | 2.73 | 12.9 | +0.7 |
| | | | | 14-21 days | | | | |
| Group 4 Smart Tab M | 6 | 14-21 | 1 × 13 mg | 16.75 | 6.97 | 2.40 | 11.3 | +0.6 |
| Group 5 Smart Tab A | 6 | 14-21 | 3 × 14 mg | 19.50 | 7.47 | 2.61 | 12.1 | −0.1 |
| Group 8 Sham Control | 6 | | — | 18.64 | 7.00 | 2.66 | 13.1 | +0.2 |

TABLE 8

| | No pigs | Days | Implant size PST | Feed intake (kgs) | Weight increase (kgs) | FCR | P2 mm | P2 mm change |
|---|---|---|---|---|---|---|---|---|
| | | | | 0-21 days | | | | |
| Group 4 Smart Tab M | 6 | 0-7 7-14 14-21 | 3 × 13 mg 1 × 1.6 mg 1 × 13 mg | 45.30 | 18.27 | 2.51 | 11.3 | +1.0 |
| Group 5 Smart Tab A | 6 | 0-7 7-14 14-21 | 3 × 14 mg 3 × 14 mg 3 × 14 mg | 53.91 | 22.73 | 2.37 | 12.1 | +1.8 |
| Group 8 Sham Control | 6 | — | — | 53.91 | 19.67 | 2.74 | 13.1 | +1.8 |

Surprisingly, for the Smart Tab M formulation, the feed conversion ratio utilising a single 13 mg implant is approximately equivalent to the daily injection regimen.

The best fat reduction (as measured by P2) is achieved utilising the Smart Tab M formulation.

It will be understood that the invention disclosed and defined in this specification extends to all alternative combinations of two or more of the individual features mentioned or evident from the text or drawings. All of these different combinations constitute various alternative aspects of the invention.

It will also be understood that the term "comprises" (or its grammatical variants) as used in this specification is equivalent to the term "includes" and should not be taken as excluding the presence of other elements or features.

The invention claimed is:

1. A sustained release apparatus comprising a plurality of sustained release mini tablet implants;
   each mini tablet implant comprising
      a pharmaceutically active composition comprising
         at least one pharmaceutically active component; and
         a carrier therefor;
   wherein the carrier is a sugar or mineral salt or mixture thereof,
   wherein each mini tablet implant is of the coated tablet type;
   each mini tablet implant being approximately 0.1 to 0.5 times the length and/or diameter of a single immediate release tablet capable of providing the desired threshold blood level depending on the pharmaceutically active component selected, and
   having a payload of approximately 30% to 70% by weight of the total payload of an equivalent immediate release treatment conducted for an equivalent period;
   the sustained release apparatus providing, in use, zero order release of pharmaceutically active component;
   each mini-tablet implant being of insufficient size and/or payload individually to provide a predetermined desired threshold blood level of pharmaceutically active component for treatment of a selected indication.

2. A sustained release apparatus according to claim 1, wherein the payload is approximately 30% to 50% by weight of that of an equivalent immediate release treatment.

3. A sustained release apparatus according to claim 1, wherein each mini tablet implant further comprises a sustained release support material, the pharmaceutically active composition being carried in or on the sustained release support material.

4. A sustained release apparatus according to claim 1, wherein each mini tablet implant takes the form of a coated compressed tablet.

5. A sustained release apparatus according to claim 1, wherein each mini tablet implant is approximately 0.20 to 0.25 times the length and/or diameter of single immediate release size tablet, capable of providing the desired threshold blood level depending on the pharmaceutically active component selected.

6. A sustained release apparatus according to claim 1, wherein each sustained release mini tablet implant is of generally circular cylindrical configuration with a cross-sectional diameter of approximately 0.1 to 4 mm and an axial length of approximately 0.1 to 20 mm.

7. A sustained release apparatus according to claim 6 wherein the axial length of each mini tablet implant is approximately 0.25 to 5 mm.

8. A sustained release apparatus according to claim 1, wherein the pharmaceutically active composition comprises at least one pharmaceutically active component selected from the group consisting of acetonemia preparations, anabolic agents, anaesthetics, analgesics, anti-acid agents, anti-arthritic agents, antibodies, anti-convulsivants, anti-fungals, anti-histamines, anti-infectives, anti-inflammatories, antimicrobials, anti-parasitic agents, anti-protozoals, anti-ulcer agents, antiviral pharmaceuticals, behaviour modification drugs, biologicals, blood and blood substitutes, bronchodilators and expectorants, cancer therapy and related pharmaceuticals, cardiovascular pharmaceuticals, central nervous system pharmaceuticals, coccidiostats and coccidiocidals, contraceptives, contrast agents, diabetes therapies, diuretics, fertility pharmaceuticals, growth hormones, growth promoters, hematinics, hemostatics, hormone replacement therapies, hormones and analogs, immunostimulants, minerals, muscle relaxants, natural products, nutraceuticals and nutritionals, obesity therapeutics, ophthalmic pharmaceuticals, osteoporosis drugs, pain therapeutics, peptides and polypeptides, respiratory pharmaceuticals, sedatives and tranquilizers, transplantation products, urinary acidifiers, vaccines and adjuvants and vitamins.

9. A sustained release apparatus according to claim 8, wherein the growth hormone is a natural or synthetic human, bovine, ovine or porcine growth hormone.

10. A sustained release apparatus according to claim 8 wherein the pharmaceutically active component comprises an anti-parasiticide which is a macrocyclic lactone or insect growth regulator, or mixtures thereof.

11. A sustained release apparatus according to claim 10 wherein the macrocyclic lactone component is ivermectin.

12. A sustained release apparatus according to claim 1, wherein the pharmaceutical carrier comprises a water-soluble substance which is in a solid state in the pharmaceutically active composition at the body temperature of an animal to which it is to be administered.

13. A sustained release apparatus according to claim 3, wherein the sustained release support material comprises a silicone material.

14. A sustained release apparatus according to claim 13, wherein the sustained release support material comprises a solid absorption medium which is selected from a fumed silica or porous silica or mixture thereof, the pharmaceutically active component being introduced into the silica.

15. A sustained release kit comprising a plurality of sustained release mini tablet implants packaged for delivery in a single treatment,
   each mini tablet implant comprising
      a pharmaceutically active composition comprising
         at least one pharmaceutically active component; and
         a carrier therefor;
   wherein the carrier is a sugar or mineral salt or mixture thereof,
   wherein each mini tablet implant is of the coated tablet type;
   each mini tablet implant being approximately 0.1 to 0.5 times the length and/or diameter of a single immediate release tablet capable of providing the desired threshold blood level depending on the pharmaceutically active component selected, and
   having a payload of approximately 30% to 70% by weight of the total payload of an equivalent immediate release treatment conducted for an equivalent period;
   the sustained release apparatus providing, in use, zero order release of pharmaceutically active component;
   each mini-tablet implant being of insufficient size and/or payload individually to provide a predetermined desired threshold blood level of pharmaceutically active component for treatment of a selected indication.

16. A sustained release kit according to claim 15, further comprising a delivery apparatus including an injector instrument for subcutaneous or intramuscular delivery of implants.

17. A sustained release kit according to claim 15, wherein the pharmaceutically active component comprises one or more selected from the group consisting of cytokines, hematopoietic factors, hormones, growth factors, neurotrophic factors, fibroblast growth factor, and hepatocyte proliferation factor; cell adhesion factors; immunosuppressants; enzymes, blood coagulating factors, proteins involved in bone metabolism, vaccines and antibodies.

18. A sustained release anthelmintic apparatus comprising a plurality of sustained release compressed mini tablet implants;
    each mini tablet implant comprising
        an anthelmintic pharmaceutical composition comprising
            an anthelmintic component; and
            a non-silicone carrier therefor and
        an anthelmintic pharmaceutical composition comprising
            at least one anthelmintic pharmaceutical component; and
            a carrier therefor;
    wherein the carrier is a sugar or mineral acid or mixture thereof,
    wherein each mini tablet implant is of the coated tablet type;
    each mini tablet implant being approximately 0.1 to 0.5 times the length and/or diameter of a single immediate release tablet capable of providing the desired threshold blood level depending on the anthelmintic pharmaceutical component selected, and
    having a payload of approximately 30% to 70% by weight of the total payload of an equivalent immediate release treatment conducted for an equivalent period;
    the sustained release apparatus providing, in use, zero order release of anthelmintic pharmaceutical component;
    each mini-tablet implant being of insufficient size and/or payload individually to provide a predetermined desired threshold blood level of pharmaceutically active component for treatment of a selected indication.

19. A sustained release anthelmintic apparatus according to claim 18, wherein the anthelmintic component comprises a macrocyclic lactone or insect growth regulator, or mixtures thereof.

20. A sustained release anthelmintic apparatus according to claim 19, wherein the macrocyclic lactone is ivermectin.

21. A method for the therapeutic or prophylactic treatment of a parasitic infection or a growth-related indication in an animal requiring such treatment, which method comprises administering to the animal a sustained release delivery apparatus comprising a plurality of sustained release mini tablet implants;
    each mini tablet implant comprising
        a pharmaceutically active composition comprising
            an anti-parasitic active or a growth-enhancing component; and
            a carrier therefor a carrier therefor;
    wherein the carrier is a sugar or mineral salt or mixture thereof,
    wherein each mini tablet implant is of the coated tablet type;
    each mini tablet implant being approximately 0.1 to 0.5 times the length and/or diameter of a single immediate release tablet capable of providing the desired threshold blood level depending on the pharmaceutical active component selected, and
    having a payload of approximately 30% to 70% by weight of the total payload of an equivalent immediate release treatment conducted for an equivalent period;
    the sustained release apparatus providing, in use, zero order release of pharmaceutical active component;
    each mini tablet implant being of insufficient size and/or payload individually to provide a predetermined required threshold blood level of pharmaceutically active component for treatment of a selected indication.

22. A method according to claim 21, wherein the animal to be treated is selected from the group consisting of sheep, cattle, goats, horses, camels, pigs, dogs, cats, ferrets, rabbits, marsupials, buffalos, yaks, primates, humans, birds including chickens, geese and turkeys, rodents including rats and mice, fish, reptiles and the like.

* * * * *